(12) United States Patent
Zhou

(10) Patent No.: US 6,356,036 B1
(45) Date of Patent: Mar. 12, 2002

(54) SYSTEM AND METHOD FOR DETERMINING BIREFRINGENCE OF ANTERIOR SEGMENT OF A PATIENT'S EYE

(75) Inventor: Qienyuan Zhou, Del Mar, CA (US)

(73) Assignee: Laser Diagnostic Technologies, Inc., San Diego, CA (US)

( * ) Notice: Subject to any disclaimer, the term of this patent is extended or adjusted under 35 U.S.C. 154(b) by 0 days.

(21) Appl. No.: 09/727,992

(22) Filed: Dec. 1, 2000

(51) Int. Cl.⁷ ................................................. A61B 3/10
(52) U.S. Cl. ...................................................... 315/215
(58) Field of Search ................................ 600/318, 319, 600/320, 321, 473, 476, 558; 351/205, 206, 215, 221

(56) References Cited

U.S. PATENT DOCUMENTS

| | | | |
|---|---|---|---|
| 3,963,019 A | 6/1976 | Quandt | 128/2 T |
| 4,735,476 A | 4/1988 | Heffner et al. | 350/96.13 |
| 4,838,683 A | 6/1989 | Ichihashi et al. | 351/221 |
| 5,209,231 A | 5/1993 | Cote et al. | 128/633 |
| 5,303,709 A * | 4/1994 | Dreher et al. | 600/476 |
| 5,565,986 A | 10/1996 | Knuttel | 356/346 |
| 5,682,240 A | 10/1997 | Redlitz | 356/349 |
| 5,787,890 A | 8/1998 | Reiter et al. | 128/665 |
| 6,112,114 A * | 8/2000 | Dreher | 600/476 |
| 6,137,585 A | 10/2000 | Hitzenberger et al. | 356/484 |

OTHER PUBLICATIONS

Publication: "Ophthalmic Interferometry". Fercher. pp. 221–228. Optics In Medicine, 1993.

Publication: "Eye Length Measurement by Laser Doppler Interferometry (LDI)". Hitzenberger et al. Satellite Conference to the 15th International Congress of the International Commission for Optics (ICO–15 SAT). pp. 232–235. Germany, Aug. 1990.

Publication: "Ophthalmic Laser Interferometry". Fercher et al. Conference on Optical Instrumentation for Biomedical Laser Applications. Austria. Apr., 1986.

Publication: "Measurement of the Axial Eye Length and Retinal Thickness by Laser Doppler Interferometry (LDI)". Hitzenberger et al. Ophthalmic Technologies. SPIE vol. 1423, pp. 46–50. 1991.

Publication: "Optical Coherence Tomography". Huang et al. Science, vol. 254. Nov., 1991.

* cited by examiner

Primary Examiner—George Manuel
(74) Attorney, Agent, or Firm—John L. Rogitz

(57) ABSTRACT

The magnitude and axial orientation of birefringence of the anterior and the posterior segments of the human eye are determined. The anterior segment includes essentially the combined birefringence of the cornea and the crystalline lens, and the posterior segment includes regions at the fundus. The optical axis and the magnitude of the birefringence of the anterior segment is first determined, then the birefringence of the posterior segment is nulled by a variable retarder. The birefringence of the posterior segment is then determined without interference of the birefringence of the anterior segment. The apparatus and method are applicable to the measurement of the birefringence of the retinal nerve fiber layer at the peripapillary region and the birefringence of the Henle fiber layer at the macular region of the retina.

18 Claims, 7 Drawing Sheets overall flow determining anterior birefring.
using blood vessel of fundus

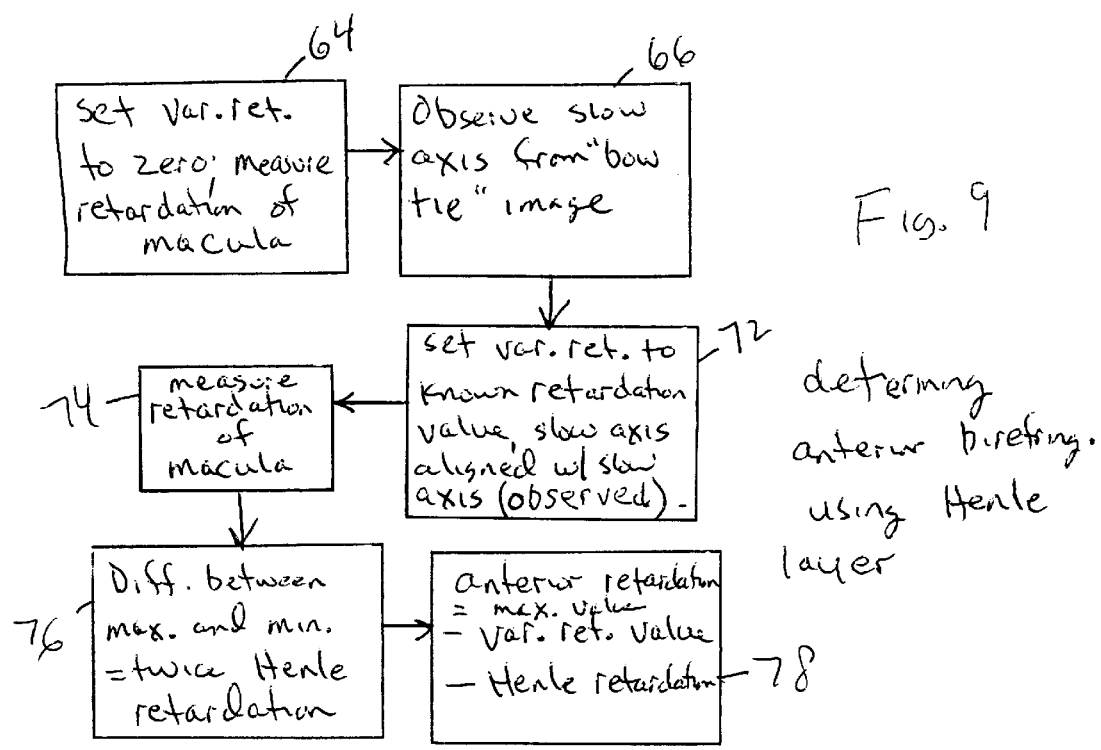
Fig. 9 determing anterior birefring. using Henle layer
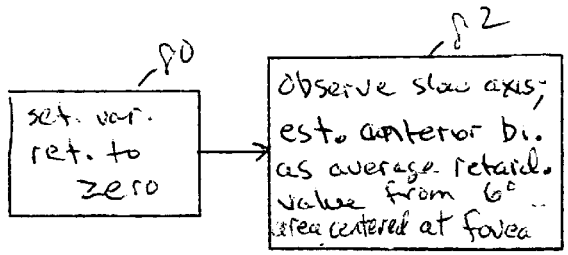
Fig. 11 using single meas.

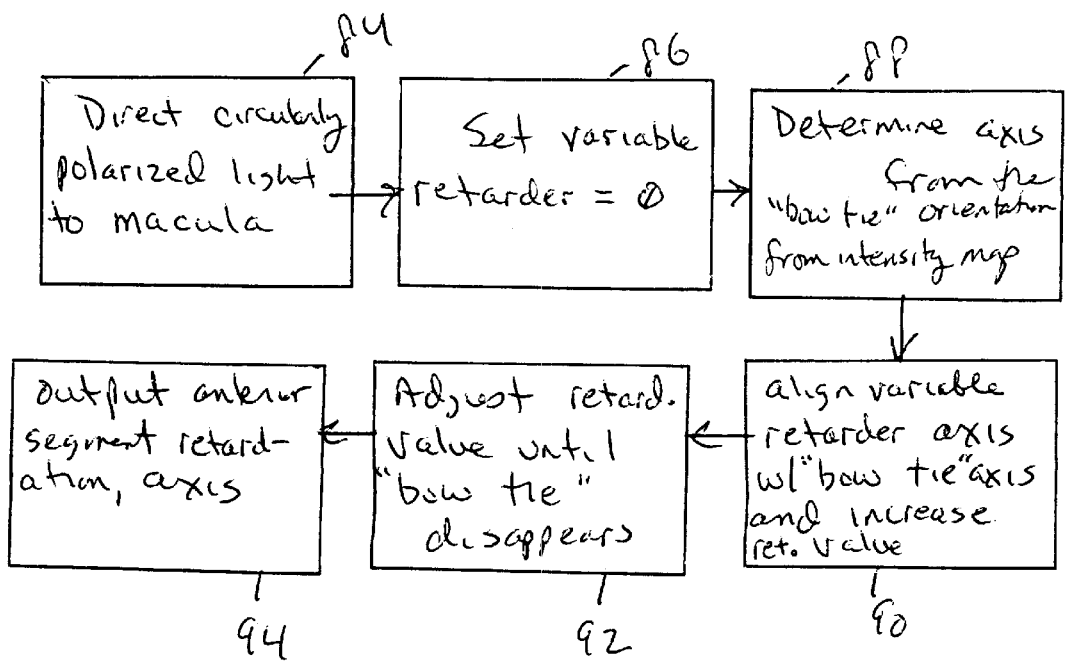

SYSTEM AND METHOD FOR DETERMINING BIREFRINGENCE OF ANTERIOR SEGMENT OF A PATIENT'S EYE

FIELD OF THE INVENTION

The present invention relates generally to diagnosing maladies of the eye using polarized light sources.

BACKGROUND

Knowing the thickness of a patient's retinal nerve fiber layer can be crucial in diagnosing glaucoma and other optic nerve diseases. It happens that the nerve fiber layer is "form birefringent", which means that, if the polarization axis of a polarized beam of light passing through the layer is neither parallel nor perpendicular to the nerve fiber bundles, retardation is introduced into the beam. More specifically, birefringence is an optical property that arises from the anisotropy of a medium through which polarized light propagates, and it is manifested by the varying of the velocity of the light, with the velocity depending on the direction of propagation and polarization axis of the light. When light propagates perpendicular to the optic axis of an anisotropic material, two orthogonally polarized components of the light, one with polarization parallel to the optic axis and the other with polarization perpendicular to the optic axis, will travel at different velocities, resulting in a phase shift between the two components. This phase shift is referred to as "retardation". The polarization state of the emerging backscattered light changes based on the amount of retardation between the two components. A retardation map can be generated based on the backscattered light that represents the thickness of the nerve fiber layer and, hence, that is useful for diagnosing maladies of the eye.

Accordingly, the present assignee has disclosed laser diagnostic devices in U.S. Pat. Nos. 5,303,709, 5,787,890, 6,112,114, and 6,137,585 that measure the thickness of the nerve fiber layer by measuring the amount of retardation of laser light in the fiber layer, with the amount of retardation then being correlated to layer thickness in accordance with principles known in the art. Likewise, as understood by the present invention the so-called Henle fiber layer, which includes photoreceptor axons and which has radially distributed slow axes centered about the fovea in the macula of the eye, is also form birefringent and consequently, its thickness also can be measured for diagnostic purposes using laser light.

As further recognized herein, however, portions of the eye (hereinafter collectively "anterior segments") that are anterior to the nerve fiber layer and Henle fiber layer are also birefringent. For instance, both the cornea and lens are birefringent. Moreover, the axial orientation and magnitude of birefringence of the anterior segments can vary significantly from person to person. Since the diagnostic beam must pass through these anterior segments, the present invention understands that the laser beam retardation caused by these portions must be accounted for, to more accurately map posterior segments such as the nerve fiber layer and Henle fiber layer.

In the above-mentioned U.S. Pat. No. 5,303,709, a corneal compensator was disclosed for neutralizing the effects of the birefringence of anterior segments of the eye on a diagnostic beam meant to measure the thickness of the nerve fiber layer. The compensating structure in the '709 patent includes a polarization sensitive confocal system attached to a scanning laser retinal polarimeter. The detector of this apparatus includes a pinhole aperture set to be conjugate with the laser source and the posterior surface of the crystalline lens so that only reflected light from the posterior surfaces of the crystalline lens is captured and analyzed. A variable retarder is then set to null any retardation in the returned light beam.

While effective for its intended purposes, the compensating features of the '709 patent, as recognized herein, require that several optical components be added to the already complex optical system of a scanning laser polarimeter. Moreover, the '709 invention uses the patient's lens as a reference surface for determining anterior segment birefringence. As recognized herein, a patient's lens reflection intensity which is captured by the confocal imaging can fluctuate due to eye movement, and consequently it can be difficult to accurately compensate for anterior segment birefringence when using the lens as a reference surface.

As also recognized herein, apart from the present invention's understanding that no method has yet been disclosed for compensating for the birefringence of anterior segments of the eye by post-measurement calculations, such post-measurement compensation can be complicated. This is because the particular contribution of the Henle fiber layer to overall retardation is not necessarily known, and instead is mixed in with the overall anterior segment birefringence.

The present invention accordingly recognizes that it would be desirable to provide a method and apparatus for measuring the birefringence of segments of the eye that are anterior to the retina, despite eye movement.

SUMMARY OF THE INVENTION

The apparatus and methods disclosed herein overcome the shortcomings of the above-mentioned corneal measurement apparatus. Instead of detecting the polarization state of the reflection from the back surface of the crystalline lens, polarimetry is performed on reflections from the fundus to determine the anterior segment retardation magnitude and axial orientation. The anterior segment birefringence is determined by analyzing the polarization state of the backscattered light from one of the following fundus regions: the macula, the major retinal vessels, and locations where the retinal birefringence is inconsequential compared to the birefringence of the anterior segment.

To do this, the present invention uses a polarized light beam of known polarization state. One of the two simple polarization states are preferred: a rotating linearly polarized light, and a circularly polarized light. A variable retarder is provided to cancel out the anterior segment birefringence so that the incident beam remains a linearly polarized light beam or circularly polarized light beam when impinging on the fundus.

With this invention, a simplified scanning laser polarimeter can use the same beam path to measure the corneal and lens birefringence as is used to measure the retinal nerve fiber layer birefringence. Also, the anterior segment birefringence can be determined without eye movement interfering with the determination. Moreover, by measuring the anterior segment birefringence along substantially identical beam paths as are used for the measuring beams of retinal nerve fiber layer, a more accurate measurement of the anterior segment birefringence can be made, since corneal birefringence varies with the incidence angle of the beam and with the location of the cornea.

As disclosed in greater detail below, the reference target used for the backscattering of the probe beam to detect birefringence of the anterior segment is not on the lens, but rather is associated with the retina. For example, the target can be the Henle fiber layer in the macula. Alternatively, major retinal blood vessels can be used as the target. This is because, as recognized herein, retinal blood vessels are close to the retinal surface and the specular reflection from the top surface of the major retinal vessels maintains the polarization state of the incident beam. As a consequence, retardation measured at major blood vessels is a measurement of the birefringence from the anterior segment. Fundus regions where the retinal birefringence is at a minimum can also be used as a reference target, because the back-scattered light from these regions preserves the polarization state of the incident light.

The output of the invention is a retardation map of the nerve fiber layer or of the Henle fiber layer (photoreceptor axon layer), which can be used as a tool to diagnose and monitor glaucoma, macular degeneration, optic neuropathy, optic neuritis, aging, and other eye diseases, such as those that cause ganglion cell or photoreceptor axon atrophy.

In one aspect, a method is disclosed for determining a birefringence of a posterior segment of an eye having an anterior segment and a retina. The method includes directing a first beam against a portion of the retina to render a first reflected beam, and based on polarization properties of the first reflected beam, determining a birefringence of the anterior segment. The method further includes configuring a polarization compensating device to null the birefringence of the anterior segment. A second beam is directed through the polarization compensating device and against a portion of the retina to render a second reflected beam. Then, based on polarization properties of the second reflected beam, the method determines a birefringence of the posterior segment.

In a preferred embodiment, the birefringence of the anterior segment is determined by configuring the polarization compensating device to have a null setting, and then directing the first beam through the device to render the first reflected beam. Next, the polarization compensating device is configured to have a non-null setting. The method once again directs the first beam through the device to render the first reflected beam.

As set forth in greater detail below, in one presently preferred embodiment, the birefringence of the anterior segment is determined by determining a maximum magnitude derived from the first reflected beam, determining a Henle fiber layer value based on a difference between the maximum magnitude and a minimum magnitude derived from the first reflected beam, and then determining a retardation value of the anterior segment by subtracting from the maximum magnitude the Henle value and a setting value of the polarization compensating device. An algorithm is also disclosed for determining the birefringence of the anterior segment. The algorithm includes determining a retardation value $\delta$ as follows: $\delta=[\lambda/360°]\sin^{-1}[I_{max}/I_{total}]^{1/2}$, wherein $I_{max}$ is a maximum output intensity of a first detector detecting the reflected beam, $I_{total}$ is the sum of the intensities output by two detectors detecting the reflected beam, and $\lambda$ is the wavelength of the first reflected beam.

The birefringence of the anterior segment alternatively can be estimated as followed. In this embodiment, a slow polarization axis of the anterior segment is observed. The method then determines a magnitude of a retardation of the anterior segment based on an average retardation value taken from a ring area centered on the fovea of the eye within a cone of 6° as measured from the pupil of the eye, where the fiber layer is relatively thin.

Circularly polarized light can be used in another embodiment. In this method, the circularly polarized light beam is directed onto the macula. A quarter wave retarder is set to zero, and then the axis of retardation is determined from the below-described "bow tie". The quarter wave retarder axis is aligned with the observed axis and its value increased from zero until the "bow tie" disappears from the image. At this point, the axis and value of the retarder represent the axis and value of the anterior segment retardation.

The details of the present invention, both as to its structure and operation, can best be understood in reference to the accompanying drawings, in which like reference numerals refer to like parts, and in which:

BRIEF DESCRIPTION OF THE DRAWINGS

FIG. 9 is a flow chart of the method for determining the anterior segment birefringence in a second embodiment using the Henle fiber layer;

FIG. 11 is a flow chart of the method for determining the anterior segment birefringence in a third embodiment using a single measurement; and FIG. 12 is a flow chart of the method for determining the anterior segment birefringence in a fourth embodiment using circularly polarized light.

DETAILED DESCRIPTION OF THE PREFERRED EMBODIMENT

As used herein, the term polarization "shifting" generically covers all types of polarization changes, including the rotation of the optical axis of polarized light, the change of linear to elliptically or circularly polarized light or vice-versa, and any combination of these. The term "polarimetry" refers to techniques for determining the polarization "shift" of a light beam. The term "polarimeter" refers to devices for performing polarimetry. The terms "spatially resolved retinal polarimetry" and "spatially resolved retinal polarimeter", refer to the technique and device for performing polarimetry, point by point, on the retina. The term "retardation map" refers to a two-dimensional display of retardation distribution measured with a spatially resolved polarimeter. The term "corneal birefringence" means anterior segment birefringence, including contributions of the lens in addition to the cornea; and the term "corneal compensator" is used to describe a device for neutralizing the birefringence of the anterior segment of the eye, such as a variable retarder.

Figure 1:
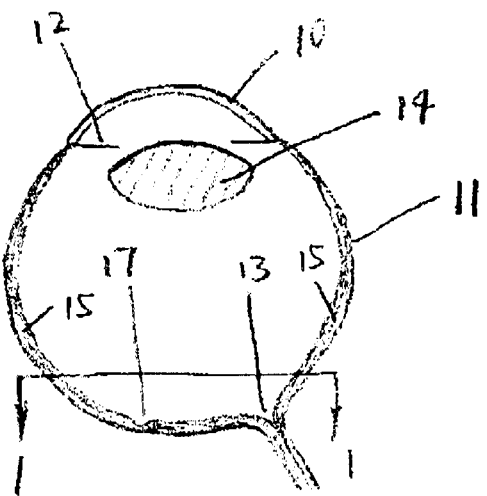
FIG. 1 is a schematic view of the eye identifying various parts of the anterior segment.
Figure 2:
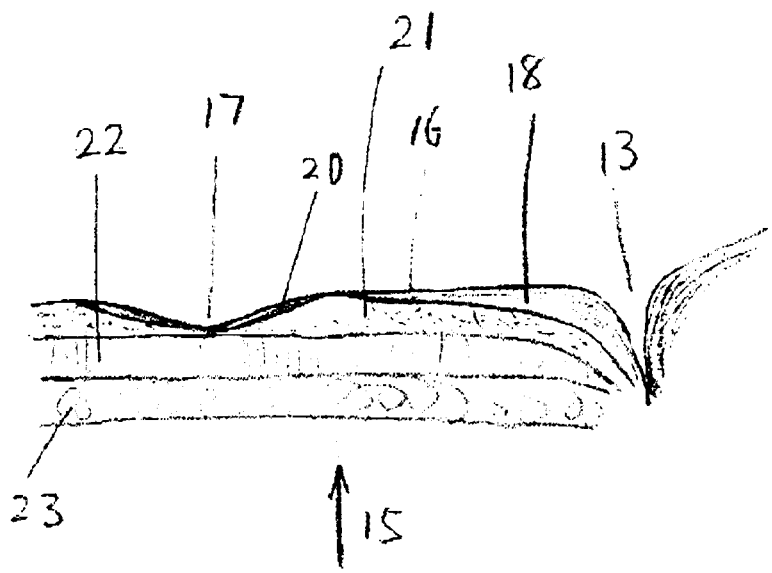
FIG. 2 is a schematic cross-sectional view of the retina as seen along the line 1—1 of FIG. 1.

Referring initially to FIGS. 1 and 2, an eye 11 has a cornea 10 that serves as the foremost, transparent portion of the eye.

Behind the cornea 10 is the iris 12 and the lens 14. The interior of the eye 11 is filled with vitreous, and at the rear of the eye is the retina 15 which is composed of the layers as illustrated in FIG. 2. The locations of the fovea 17 and the optic nerve head 13 are also shown in FIG. 1.

As shown in FIG. 2, the retina 15 includes an inner limiting membrane 16, followed by the nerve fiber layer 18, the receptor system 21, the Henle fiber layer 20, the retinal pigment epithelium 22, and the choroid 23. All eye structure anterior to the inner limiting membrane 16 is referred to herein as the "anterior segment" of the eye.

Figure 3:
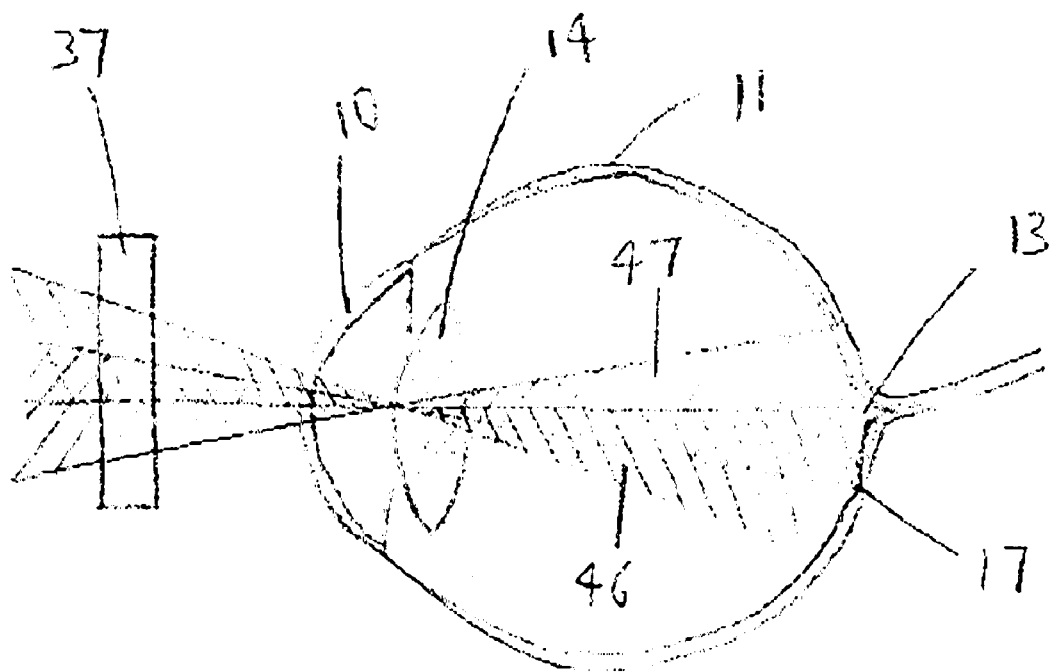
FIG. 3 is a schematic diagram showing the scan beam paths in the eye.

As set forth further below, the thickness of the Henle fiber layer 20 and nerve fiber layer 18 can be measured. FIG. 3 illustrates the different beam paths that can be used to undertake these measurements. Specifically, the scan beam path in the eye is shown at 46 to be centered on the fovea 17 for macula measurement, whereas the scan beam path shown at 47 is centered on the optic nerve head 13 for peripapillary nerve fiber layer measurement. These measurement zones are adjacent to each other and are substantially overlapping. As recognized by the present invention, substantially the same region of the cornea and that of the lens are used in both measurements. Consequently, the effect of the anterior segment is substantially same in both measurements.

Figure 4:
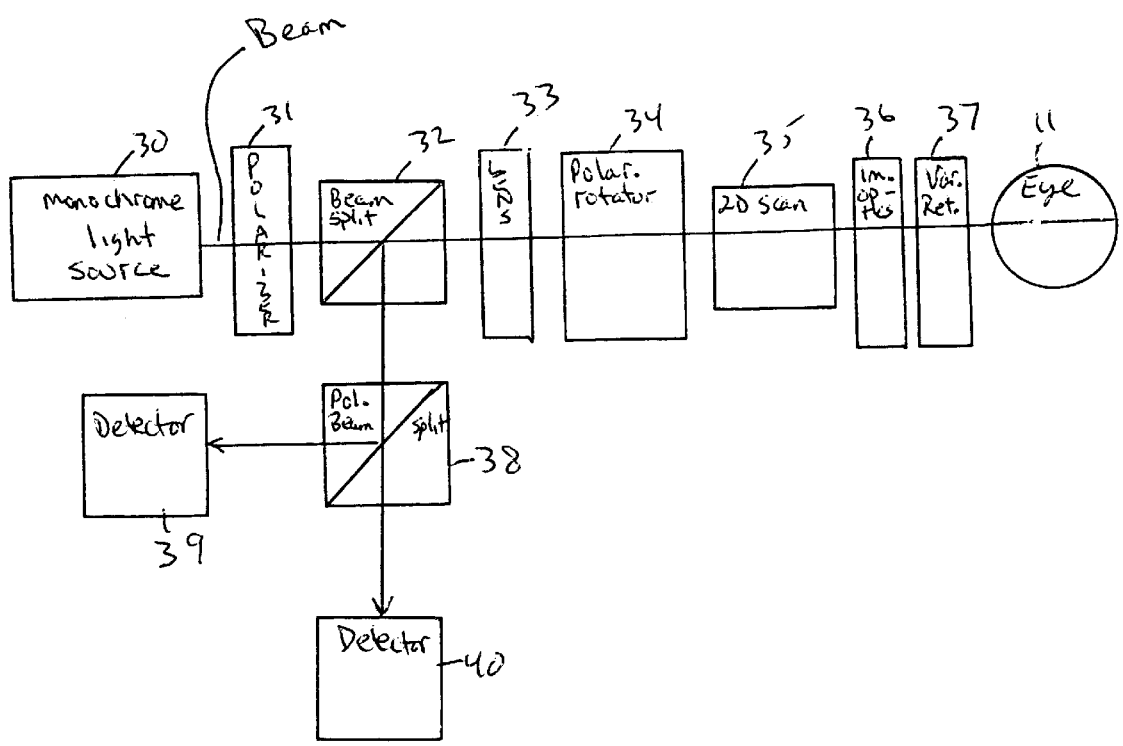
FIG. 4 is a block diagram of an optical system in accordance with the present invention.

FIG. 4 shows one optical system that can be used to undertake the present invention. A monochromatic light source 30, such as a laser, generates a monochromatic light beam indicated by the line labelled "beam". The beam passes through a polarizer 31 to polarize the light, the polarization axis of which is set either parallel or perpendicular to the incidence plane of a non-polarizing beam splitter 32. The light beam is then collimated by a lens 33. The collimated beam passes through a polarization rotator 34, which rotates the polarization axis of the beam by an angle $\theta$ while the light beam remains linearly polarized.

From the rotator 34, the polarized light propagates through a scanning unit 35. In one preferred embodiment, the scanning unit 35 includes a two dimensional scanning device. An appropriate conventional two dimensional scanning unit can be used. In one embodiment, a first line scanner performs a line scan and a second scanner performs step scan at the completion of each line scan. The two-dimensional scan field generated thereby is then projected through an imaging optics unit 36, which can include an objective lens and a focusing unit to compensate for the refraction error of the eye.

The beam next passes through a variable retarder 37. As set forth further below, the variable retarder 37 is an example of a corneal compensator that is used to measure the birefringence of the anterior segment of the eye. Also, the variable retarder 37 serves as a compensator to neutralize the anterior segment birefringence of the eye. The variable retarder 37 can be a liquid crystal variable retarder with controlled axes or it can be configured with two zero order fixed retarders.

Backscattered light, i.e., reflections from the fundus, propagates back through the same optical components until it is redirected by the beam splitter 32 towards a polarizing beam splitter 38. The polarizing beam splitter 38 separates the light into two components. One component with a polarization axis perpendicular to the incidence plane of the beam splitter 38 is reflected to a first detector 39, and the other component with polarization axis parallel to the incidence plane is transmitted to a second detector 40.

Figure 5:
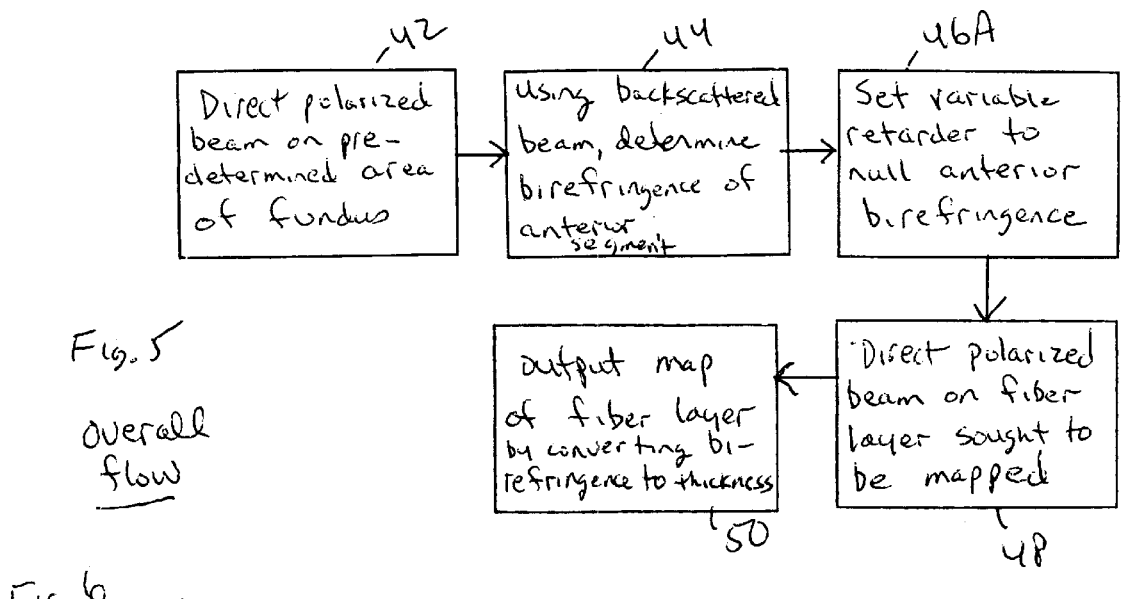
FIG. 5 is a flow chart of the overall method of the present invention.

Now referring to FIG. 5, the overall method steps for measuring the birefringence (as manifested in the light beam retardation it causes) of the anterior segment can be seen. Commencing at block 42, the polarized light beam is directed onto a predetermined area of the fundus. More generally, the beam is directed onto the retina.

Moving to block 44, the backscattered beam is used to determine the birefringence of the anterior segment, in accordance with disclosure below. Then, at block 46A the variable retarder 37 is set to a value and axis that nulls the anterior birefringence. Next, at block 48 polarized light is directed on the fiber layer sought to be mapped, e.g., on the nerve fiber layer 18 or Henle fiber layer 20. This causes backscattered light to be collected, with the backscattered light representing only the retardation caused by posterior segments, since the anterior segment birefringence is nulled by the variable retarder 37. At block 50, a layer thickness map is output by converting the birefringence values to layer thickness values in accordance with principles known in the art.

Figure 6:
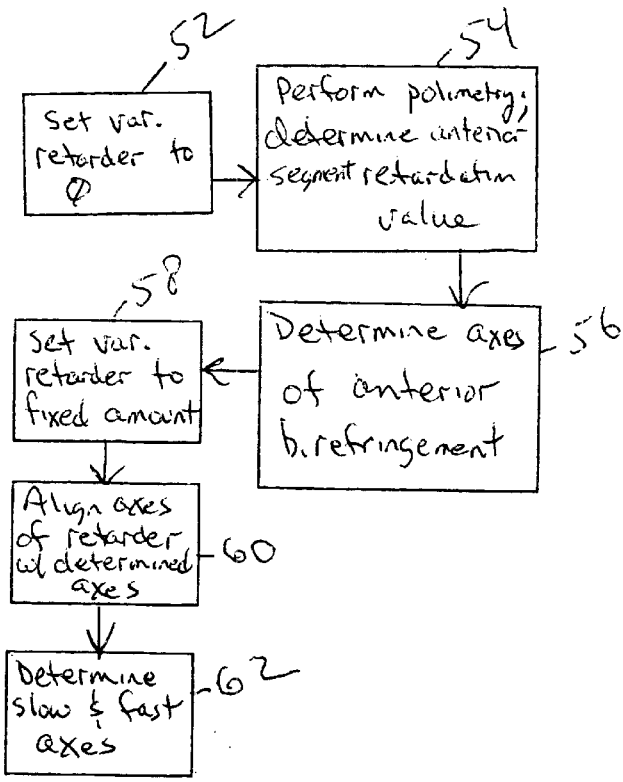
FIG. 6 is a flow chart of the method for determining the anterior segment birefringence in a first embodiment using retinal blood vessels or predetermined areas of the fundus.

FIG. 6 shows a first method for determining the birefringence of the anterior segment, using retinal blood vessels or non-birefringent portions of the fundus. Commencing at block 52, the variable retarder is set to a value of zero. Moving to block 54, polarimetry is undertaken by directing the light beam against retinal blood vessels or non-birefringent portions of the fundus.

Figure 7:
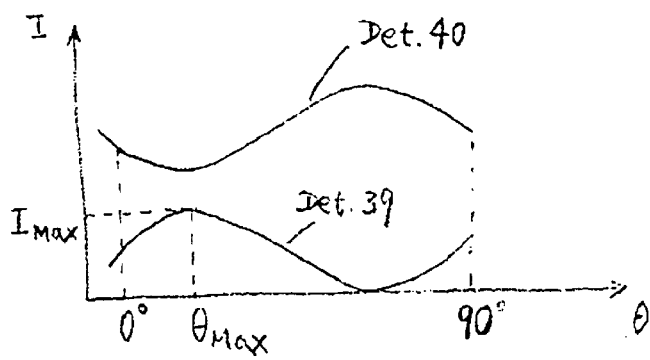
FIG. 7 is a graph illustrating the relationship between detector outputs and the polarization axis.

It is useful to note here that if the polarizer 31 is set with its axis parallel to the incidence plane of the beam splitter 32, then the first detector 39 receives the cross-polarized light and the second detector 40 receives the light of the original polarization state. The output of detector 39 and detector 40 both depend on the retardation and the axis of polarization. FIG. 7 shows the relationship between the output of the two detectors and the linear polarization axis. In FIG. 7, "$\theta$" is the orientation of the linear polarization after the rotator 34. The retardation value $\delta$ is calculated at block 54 using the following formula:

$\delta = [\lambda/360°]\sin^{-1}[I_{max}/I_{total}]^{1/2}$, wherein $I_{max}$ is the maximum output intensity of the first detector 39, $I_{total}$ is the total intensity of output by the detectors 39, 40, and $\lambda$ is the wavelength of the beam.

Note that, in the event of eye movement or lens accommodation, the light beam intensity would fluctuate. However, $I_{max}$ and $I_{total}$ would fluctuate proportionately, hence, the value of $\delta$ is not affected by eye movement accommodation.

Figure 8:
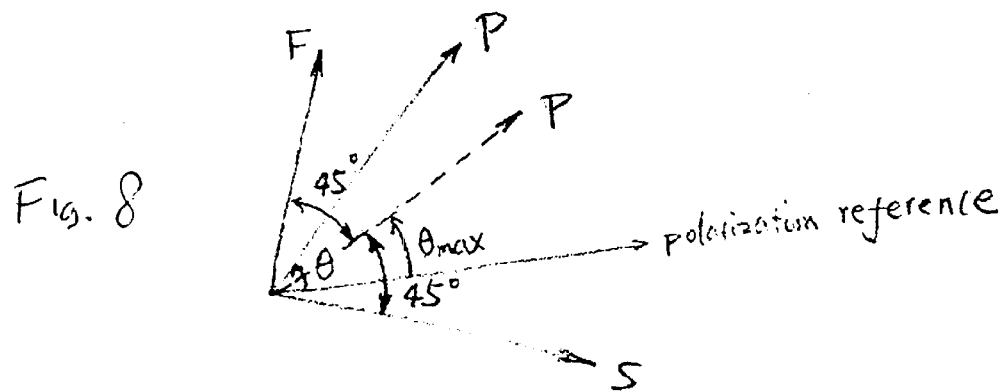
FIG. 8 is a schematic view illustrating the relationship between the polarization axis and retarder axes.

It is to be understood that the angle $\theta_{max}$ is the polarization axis corresponding to $I_{max}$ and is 45° from either the slow or fast axis of the retardation of the beam. The relationship between the various axes can be appreciated in reference to FIG. 8, wherein F and S stand for the fast and slow axis of the retardation, respectively, P represents the axis of the linear polarized light, $\theta$ is the angle of rotation of the linear polarization, and $\theta_{max}$ is the polarization axis corresponding to $I_{max}$ of the first detector 39 as defined in FIG. 8. Retardation axes are determined at block 56 in FIG. 6 by shifting the polarization by $\theta_{max}$ as shown in FIG. 8 and then adding and subtracting 45° therefrom.

It must then be determined which retardation axis is the fast axis and which is the slow. Accordingly, continuing the process of determining the fast and slow axes of the anterior segment birefringence in FIG. 6, at block 58 the value of the variable retarder is set to a predetermined bias value. At block 60, the axes of the variable retarder 37 are aligned with the axes of the original retarder. At block 62, if the maximum of the detector 39 output is higher than it was before the addition of the bias, it is thereby determined that the slow axis of the bias retarder is aligned with the slow axis before the bias. On the other hand, if the maximum of the detector 39 output is lower, the slow axis of the bias retarder is aligned with the fast axis.

Now referring to FIG. 9, the method for measuring anterior segment birefringence using the Henle fiber layer 20 can be seen. Commencing at block 64, the value for the variable retarder 37 is set to zero, and the value of the retardation of the macula (i.e., retardation caused by the Henle fiber layer in the macula) is measured in accordance with the following disclosure.

Figure 10:
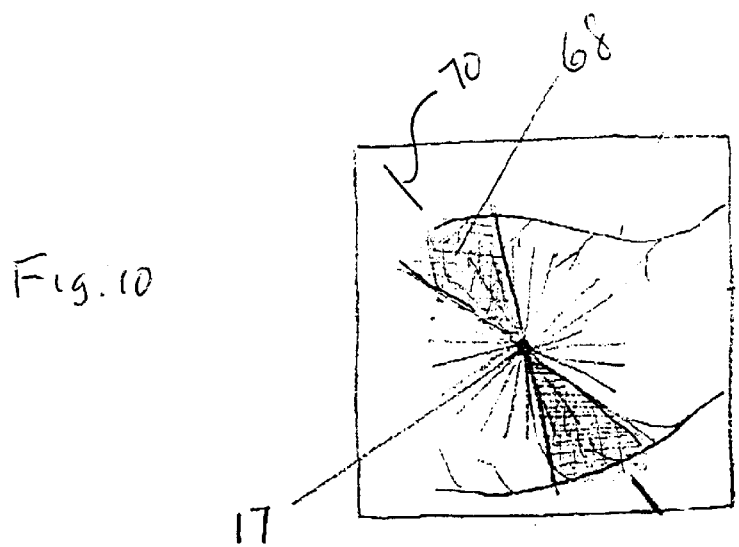
FIG. 10 is a schematic illustration of the appearance of the retardation distribution of the Henle fiber layer.

As recognized herein, the slow axis of the birefringence of the Henle fiber layer 20 is parallel to the axons and is therefore radially distributed. Accordingly, at block 66 in FIG. 9 and as shown best at reference numeral 68 in FIG. 10, a bow-tie pattern is usually observed. The bow-tie pattern is a result of the combined retardation of the anterior segment of the eye 11 and the variable retarder 37 superimposed onto the uniformly distributed retardation of the Henle fiber layer. The orientation where the bow-tie pattern is brightest, indicated at 70 in FIG. 10, corresponds to the slow axis of the combined retardation. In contrast, the orientation of where the bow-tie pattern is darkest corresponds to the fast axis. When the combined retardation of the anterior segment and the variable retarder is zero, the bow-tie pattern disappears and the macula consequently exhibits a uniform retardation map. Thus, the fast and slow axes of the combined retardation can be determined immediately from observing the bow-tie pattern at block 66.

However, the magnitude of the combined retardation cannot be determined from a single Henle fiber layer measurement because the retardation of the Henle fiber layer is unknown. Therefore, the logic moves to block 72 in FIG. 9, wherein the variable retarder 37 set to a known value and the slow axis of the variable retarder 37 is aligned with the slow axis of the anterior segment birefringence observed at block 66. Proceeding to block 74, the light beam is directed against the Henle fiber layer 20 of the macula, and the retardation of the anterior segment is then sampled from a ring area centered on the fovea 17 where the bow-tie pattern has maximum modulation (i.e. where the Henle fiber layer is thickest). The difference between the maximum and minimum of the measured values is two times the retardation of the Henle fiber layer, and this is determined at block 76. At block 78, the anterior segment retardation is determined by subtracting from the maximum value both the retardation of the Henle fiber layer and the set retardation value of the variable retarder 37.

Now referring to FIG. 11, a method for estimating the anterior segment birefringence using a single measurement is illustrated. Commencing at block 80, the variable retarder 37 is set to zero. Then, at block 82 the light beam is directed against the Henle fiber layer and the slow axis of the anterior segment is observed per the above discussion. The magnitude of the retardation of the anterior segment is estimated as being the average retardation value taken from an area centered at the fovea 17 where the Henle fiber layer is relatively thin anywhere in 6° as measured from the center of the pupil.

FIG. 12 shows yet another embodiment for using circularly polarized light as the probing beam. It is to be understood that when circularly polarized is used, the system shown in FIG. 4 is modified as follows. The variable retarder 37 is replaced with a quarter-wave retarder to generate a circularly polarized light beam. The axes of the quarter-wave retarder are offset 45° from the axis of the linearly polarized light. In this embodiment, the second detector 40 receives the cross-polarized light and the first detector 39 receives the light of the original polarization state. The macular intensity image generated by the second detector 40 is used to determine the anterior segment birefringence.

The method for using circularly polarized light begins at block 84, wherein a circularly polarized light beam is directed onto the macula. The variable retarder is set to zero at block 86, and then the axis of retardation is determined at block 88 from the resulting "bow tie" image, with the intensity map being used in lieu of the birefringence map. Moving to block 90, the variable retarder axis is aligned with the observed axis and its value increased from zero while maintaining its axis alignment until, at block 92, the "bow tie" disappears from the image. At this point, the axis and value of the variable retarder represent the axis (exactly crossed) and a value that is equal to that of the anterior segment retardation. Accordingly, these values are output at block 94 as representing the axis and value of the anterior segment retardation.

Once the anterior segment retardation and axis are determined, the retarder is set to neutralize the corneal birefringence as discussed above. The retardation map of the nerve fiber layer and/or the Henle fiber layer is then accurately measured, and the thickness of these structure can be estimated.

While the particular SYSTEM AND METHOD FOR DETERMINING BIREFRINGENCE OF ANTERIOR SEGMENT OF A PATIENT'S EYE as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more". All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. §112, sixth paragraph, unless the element is expressly recited using the phrase "means for" or, in the case of a method claim, the element is recited as a "step" instead of an "act".

I claim:

1. A method for analyzing the birefringence of the anterior and the posterior segments of an eye, comprising:

providing a light beam with a known polarization state;

directing the light beam through the anterior segment of the eye such that the light beam impinges on a selectable region of the fundus and reflects therefrom to establish a return beam;

based on the return beam, determining an optical axis and magnitude of an anterior segment birefringence;

configuring a variable retarder to null the anterior segment birefringence; and determining a birefringence of the posterior segment by directing a beam through the variable retarder and the posterior segment.

2. The method of claim 1, wherein the selectable region of the fundus comprises at least one object at the fundus which preserves the polarization of the incident light beam after reflection from the object, the object including at least one of: blood vessels, and regions at the fundus having a birefringence substantially smaller than the anterior segment birefringence.

3. The method of claim 1, wherein the region of the fundus comprises eye tissues that have birefringence distributed radially from a center around the fovea of the eye.

4. The method of claim 1, wherein the posterior segment comprises at least one of: optic nerve fiber layer, and Henle fiber layer.

5. The method of claim 1, further comprising detecting the return beam using at least two polarization sensitive detectors.

6. The method of claim 1, wherein the light beams travel along respective first and second paths, and the first and second paths are substantially overlapping.

7. A method for analyzing the birefringence of anterior and posterior segments of an eye, comprising:
generating an incident light beam with a known polarization state along a beam path;
positioning a variable retarder in the beam path;
directing the incident light beam through the anterior segment of the eye, the incident light beam impinging upon and reflected from a selectable region of the fundus to establish a reflected beam;
directing the reflected beam to a polarization beam splitter, and separating the reflected beam into two orthogonally polarized components;
generating signals using respective polarization sensitive detectors from the orthogonally polarized components; and
analyzing the signals in accordance with the polarization and birefringent characteristics of the selectable region.

8. The method of claim 7, wherein the orthogonally polarized components comprise either linearly polarized light beams or circularly polarized light beams.

9. The method of claim 7, wherein the selectable region of the fundus comprises at least one object at the fundus which preserves the polarization of the incident light beam in the reflected light beam, the object including at least one of: blood vessels, and regions at the fundus having a birefringence substantially smaller than the birefringence of the anterior segment.

10. The method of claim 7, wherein the selectable region of the fundus comprising optical tissues having birefringence distributed radially from a center around the fovea of the eye.

11. The method of claim 7, further comprising determining a thickness measurement of birefringent material at the selectable region.

12. The method of 11, further comprising diagnosing at least one of: (a) aging, (b) macular degeneration, (c) glaucoma, (d) optic neuropathy, and (e) optic neuritis, based on the thickness measurement.

13. A method for determining a birefringence of a posterior segment of an eye having an anterior segment and a retina, comprising:
directing a first beam against a portion of the retina to render a first reflected beam;
based on polarization properties of the first reflected beam, determining a birefringence of the anterior segment;
configuring a polarization compensating device to null the birefringence of the anterior segment;
directing a second beam through the polarization compensating device and against a portion of the retina to render a second reflected beam; and
based on polarization properties of the second reflected beam, determining a birefringence of the posterior segment.

14. The method of claim 13, wherein the act of determining a birefringence of the anterior segment further comprises:
configuring the polarization compensating device to have a null setting;
directing the first beam through the device to render the first reflected beam;
configuring the polarization compensating device to have a non-null setting; and
once again directing the first beam through the device to render the first reflected beam.

15. The method of claim 13, wherein the act of determining a birefringence of the anterior segment further comprises:
determining a maximum birefringence magnitude derived from the first reflected beam;
determining a Henle fiber layer value based on a difference between the maximum birefringence magnitude and a minimum birefringence magnitude derived from the first reflected beam; and
determining a retardation value of the anterior segment by subtracting from the maximum magnitude the Henle fiber layer value and a setting value of the polarization compensating device.

16. The method of claim 13, wherein the act of determining a birefringence of the anterior segment further comprises:
determining a retardation value $\delta$ as follows:
$\delta=[\lambda/360°] \sin^{-1}[I_{max}/I_{total}]^{1/2}$, wherein $I_{max}$ is a maximum output intensity of a first detector detecting the first reflected beam, $I_{total}$ is a total intensity output by plural detectors detecting the first reflected beam, and $\lambda$ is the wavelength of the first reflected beam.

17. The method of claim 13, wherein the act of determining a birefringence of the anterior segment further comprises:
directing a light beam of known state to the macula area;
observing a slow polarization axis of the anterior segment from an intensity map; and
determining a magnitude of a retardation of the anterior segment based on an average retardation value taken from a ring area centered on the fovea of the eye within a cone of 6° as measured from the pupil of the eye where the birefringence fiber layer is relatively thin.

18. A method for using a circularly polarized light beam to measure anterior segment retardation, comprising:
directing the beam onto the macula;
setting a variable retarder to zero;
determining an axis of retardation;
aligning an axis of the variable retarder with the axis of retardation;
increasing the variable retarder from zero until a predetermined image is generated, at which point the axis and value of the variable retarder represent the axis and value of the anterior segment retardation.

* * * * *